(12) United States Patent
Kim et al.

(10) Patent No.: US 9,005,583 B2
(45) Date of Patent: Apr. 14, 2015

(54) CHAIN-END FUNCTIONALIZED POLY(ETHYKENE OXIDE) AND PROCESS FOR THE PREPARATION OF A NANO-SIZED TRANSITION METAL OR METAL SALT USING THE SAME

(75) Inventors: Jungahn Kim, Seoul (KR); Kwang Ung Kim, Seoul (KR); Seung Sang Hwang, Seoul (KR); Soon Man Hong, Seoul (KR); Soonjong Kwak, Seoul (KR); Joon Hyeong Park, Seoul (KR); Ji Hee Kim, Gyeonggi-do (KR); Dong Youn Shin, Seoul (KR); Soon Geun Hwang, Gyeonggi-do (KR); Jang Seop Kim, Seoul (KR); Han Wook Ryu, Seoul (KR)

(73) Assignee: Youl Chon Chemical Co., Ltd., Seoul (KR)

( * ) Notice: Subject to any disclaimer, the term of this patent is extended or adjusted under 35 U.S.C. 154(b) by 1965 days.

(21) Appl. No.: 11/994,964

(22) PCT Filed: Jul. 6, 2006

(86) PCT No.: PCT/KR2006/002644
§ 371 (c)(1),
(2), (4) Date: Jul. 15, 2008

(87) PCT Pub. No.: WO2007/007976
PCT Pub. Date: Jan. 18, 2007

(65) Prior Publication Data
US 2009/0142268 A1    Jun. 4, 2009

(30) Foreign Application Priority Data
Jul. 7, 2005    (KR) .................. 10-2005-0061072

(51) Int. Cl.
| | | |
|---|---|---|
| A61B 5/055 | (2006.01) | |
| C08G 65/329 | (2006.01) | |
| A61K 49/00 | (2006.01) | |
| C08G 65/32 | (2006.01) | |
| A61K 47/48 | (2006.01) | |

(52) U.S. Cl.
CPC .......... *C08G 65/32* (2013.01); *A61K 47/48215* (2013.01)

(58) Field of Classification Search
CPC ....... A61K 9/00; A61K 9/002; A61K 9/0082; A61K 9/0063
See application file for complete search history.

(56) References Cited

U.S. PATENT DOCUMENTS

| | | | | |
|---|---|---|---|---|
| 3,476,697 | A * | 11/1969 | Clements ...................... | 525/438 |
| 4,483,969 | A * | 11/1984 | Joyner et al. .................. | 525/437 |
| 6,440,565 | B1 | 8/2002 | Kim et al. | |
| 6,530,944 | B2 * | 3/2003 | West et al. ...................... | 607/88 |
| 6,692,724 | B1 * | 2/2004 | Yang et al. .................... | 424/1.49 |
| 7,319,127 | B2 | 1/2008 | Kim et al. | |
| 2004/0033345 | A1 * | 2/2004 | Dubertret et al. ............. | 428/220 |

FOREIGN PATENT DOCUMENTS

| | | |
|---|---|---|
| EP | 0497404 A1 | 8/1992 |
| EP | 1388561 A2 | 2/2004 |
| KR | 10-2001-0068945 A | 7/2001 |
| KR | 10-0453131 A | 2/2004 |
| KR | 1020040034064 A | 4/2004 |

OTHER PUBLICATIONS

Topp, M.D.C., et al., "Quai-Living POlymerization of N-Isopropylacrylamide onto Polyethylene Glycol", 2000, 33, pp. 4986-4988.*
Ranger, M., et al., "From Well-Defined Diblock Copolymers Prepared ... ", 2001, Journal of Polymer Sceince, 39, pp. 3861-3874.*
Park, J., "Synthesis of folate-linked PEO and its use for the preparation of nano-sized cadmium sulfide", 2004, 29(2), p. 1-2.*
Pramanick, D., et al., "Copolyester of Trmellitic Acid ... ", 2004, Journal of Applied POlymer Science, 91, pp. 343-346.*
K. Mallik, Polymer Stabilized Silver Nanoparticles: A Photochemical Synthesis Route, Journal of Materials Science, vol. 39, 2004, pp. 4459-4463.
J.M. Harris, Laboratory Synthesis of Polyethylene Glycol Derivatives, Journal of Macromolecular Science—Reviews in Macromolecularchemistry, Marcel Dekker Journals, vol. C-25, No. 3, Jan. 1, 1985, pp. 325-373.
J. harris et al.; "Effect of Pegylation on Pharmaceuticals" Nature reviews vol. 2, Mar. 2003, pp. 214-221.
Samuel Zalipsky, "Functionalized Poly(ethylene glycol) for Preparation of Biological Relevant Conjugates" Bioconjugate Chem. 1995, 6, 150-165.
Slomkowski et al., "Anionic Ring-Opening Polymerization" Center of Molecular and Macromolecular studies, Polish Academy of Sciences, Sienkiewicza 112, 90-393 pp. 88-122.
Quirk et al."Macromonomers and Macroinitiators" Institute of Polymer Science, University of Akron, Ohio 44325, and Jungahn Kim, Polymer Processing laboratory, Korea institute of Science and Technology pp. 264-289.
Jankova et al."Synthesis of Amphiphillic PS-b-PEG-b-PS by Atom Transfer Radical Polymerization" Macromolecules 1998, 31, 538-541.
Topp et al. "Thermsensitive Mice-Forming Block Copolymers of Poly(ethylene glycol) and Poly(N-isopropylacrylamide)" Macromolecules 1997, 30 8518-8520.
Brondsted et al."pH-Sensitive Hydrogels" American Chemical Society 1992 p. 284-305.

* cited by examiner

*Primary Examiner* — Michael G Hartley
*Assistant Examiner* — Lance Rider
(74) *Attorney, Agent, or Firm* — Browdy and Neimark, PLLC

(57) ABSTRACT

There is provided a novel chain-end functionalized PEO of formulas (I) to (IV) prepared via living anionic polymerization and chain-end functionalization, as well as a simple method of preparing nano-sized transition metal or metal salt particles using the same, which can be readily stabilized even in an aqueous medium. The water-soluble PEO-based polymers having various functional groups (including a drug group such as vitamin and anti-cancer agent) and the process of preparing nano-sized transition metal or metal salt particles using the same can be advantageously used in the development of new materials for drug delivering system and imaging, e.g., a contrast agent and an anti-cancer agent simultaneously.

9 Claims, No Drawings

CHAIN-END FUNCTIONALIZED POLY(ETHYKENE OXIDE) AND PROCESS FOR THE PREPARATION OF A NANO-SIZED TRANSITION METAL OR METAL SALT USING THE SAME

TECHNICAL FIELD

The present invention relates to a chain-end functionalized poly(ethylene oxide) (PEO) and a process of preparing a nano-sized transition metal or metal salt using the same. More particularly, the present invention relates to a novel chain-end functionalized PEO prepared via living anionic polymerization of ethylene oxide and chain-end functionalization of the resulting polymer, as well as a simple method of preparing nano-sized transition metal or metal salt particles using the same that can be readily stabilized in aqueous media.

BACKGROUND ART

Various methods for functionalizing the chain-end of PEO, which is useful for capsulating water-insoluble drugs, and their applications have been studied for a long time (Harris et al, Nature Reviews Drug Discovery, 2003, Vol. 2, pages 214-221; Zalipsky et al, Bioconjugate Chemistry, 1995, Vol. 6, pages 150-165). In this respect, the processes for preparing PEO such as poly(ethylene glycol) by living anionic polymerization are well described in various literatures (e.g., Slomkowski et al, "Anionic Ring-opening Polymerization", in Ring-Opening Polymerization: Mechanism, Catalysis, Structure, Utility, Edited by D. J. Brunelle, 1993, Chap. 3, pages 87-128; Quirk et al, "Macromonomers and Macromonomers", in Ring-Opening Polymerization: Mechanism, Catalysis, Structure, Utility, Edited by D. J. Brunelle, 1993, Vol. 9, pages 263-293).

Further, the process for preparing block copolymers consisting of PEO and other polymers are also disclosed in various literatures (e.g., Jankova et al, Macromolecules, 1998, Vol. 31, pages 538-541; Topp et al, Macromolecules, 1997, Vol. 30, pages 8518-8520). In particular, it has been well known that a micelle prepared by using a block copolymer consisting of PEO and poly(N-isopropylacrylamide) (PNiPAM) exhibits thermo-responsive property.

On the other hand, polymeric electrolytes prepared by polymerizing vinylic monomers having a carboxylic acid, sulfonic acid, amine or ammonium group have been used as pH-responsive hydrogels (Harland et al, "Polyelectrolyte Gels, Properties, Preparation, and Applications," ACS Symp. Series # 480, Am. Chem. Soc, 1992, Chap. 17, page 285).

However, the conventional methods are disadvantageous since they must perform a number of reaction steps. For example, the step of protecting one chain-end of PEO with a functional group such as a methyl group has to be carried out prior to the functionalization step of the other chain-end of PEO, thereby causing a low yield.

DISCLOSURE

Technical Problem

Therefore, it is an object of the present invention to provide chain-end functionalization processes of living PEO synthesized via living anionic polymerization manner for effectively preparing various polymeric pro-drugs from the reaction of the functionalized PEO with drugs and for capsulating a water-insoluble drug and increasing drug-permeability as well as maintaining drug-effect.

Further, it is another object of the present invention to provide a simple method of preparing transition metal or metal salt particles using the chain-end functionalized PEO obtained by said process.

Technical Solution

In accordance with one aspect of the present invention, there is provided a chain-end functionalized PEO selected from the group consisting of compounds of formulas (I) to (IV):

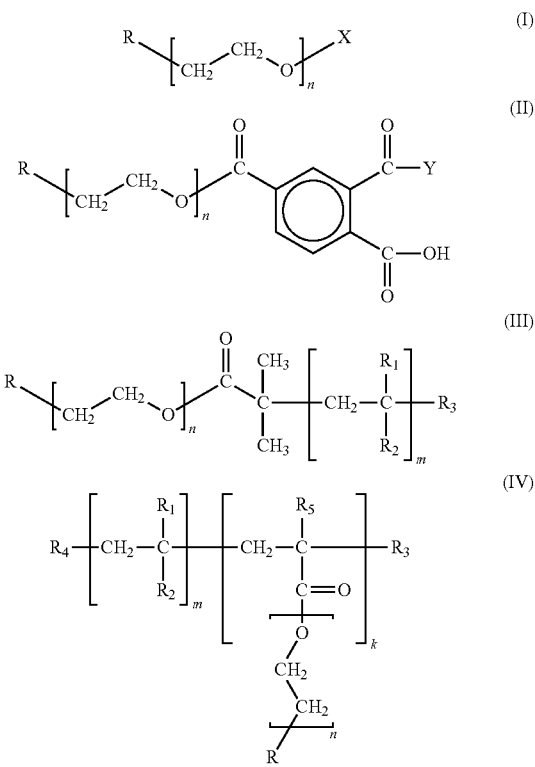

wherein,
R is methyl, n-butyl, sec-butyl or tert-butyl,
$R_1$ and $R_5$ are each independently hydrogen or methyl,
$R_2$ is an amide group having a functional group selected from the group consisting of N-isopropylacrylamide, sulfabenzene, sulfioxazole, sulfacetamide, sulfamethizole, sulfadimethoxine, sulfadiazine, sulfamethoxy pyridazine, sulfamethazine, sulfisoimidine, sulfapyridine, indisulam and amprenavir,
$R_3$ is hydrogen, isobutylacrylonitryl, phenyl or halogen,
$R_4$ is phenyl or isobutylacrylonitryl,
X is hydrogen, propylene sulfonic acid, 2-bromoisobutyryl, 2-bromopropionyl, propylene sulfide, methacrylamide or phthalic anhydride,
Y is sulfonamide group such as sulfabenzene, sulfioxazole, sulfacetamide, sulfamethizole, sulfadimethoxine, sulfadiazine, sulfamethoxy pyridazine, sulfamethazine, sulfisoimidine, sulfapyridine, indisulam or amprenavir; vitamine group such as folic acid; or drug group such as doxorubicin, paclitaxel or vancomycin;
n is an integer in the range of 10 to 500,
k is an integer in the range of 1 to 10, and
m is an integer in the range of 5 to 50.

In accordance with another aspect of the present invention, there is provided a process of preparing a nano-sized transition metal or metal salt, comprising: a) providing PEO having a number-average molecular weight of 500 to 100,000 g/mol, preferably 1,000 to 20,000 g/mol, by living anionic polymerization of ethylene oxide using an alkyl lithium as an initiator; b) reacting the living PEO obtained in step a) with a functional material under high vacuum to obtain a compound of formula (I) or (II); c) among the compounds obtained in step b), reacting the compound of formula (I) wherein X is 2-bromoisobutyryl, 2-bromopropionyl or methacrylamide with N-isopropyl acrylamide or sulfonamide methacrylamide monomer in a solvent using a radical polymerization technique to obtain a graft or block copolymer of formula (III) or (IV); and d) reacting the chain-end functionalized PEO-based polymer obtained in step b) or c) with an aqueous metal salt solution in the presence of a reducing agent to obtain the polymer-stabilized transition metal or metal salt particles having a size ranging from 1 to 500 nm.

Best Mode

Preferred examples of the present invention will now be described in detail.

The present invention relates to a novel polymer-drug material such as a PEO-based polymer, and graft or block copolymer selected from the group consisting of compounds of formulas (I) to (IV), wherein various functional materials (e.g., vitamins and drugs such as an anti-cancer agent) are attached to the chain-end of PEO having a number-average molecular weight of 500 to 100,000 g/mol. Further, the present invention relates to a method of preparing nano-sized transition metal or metal salt particles using said chain-end functionalized polymer, wherein the particles are stabilized in the polymer matrix.

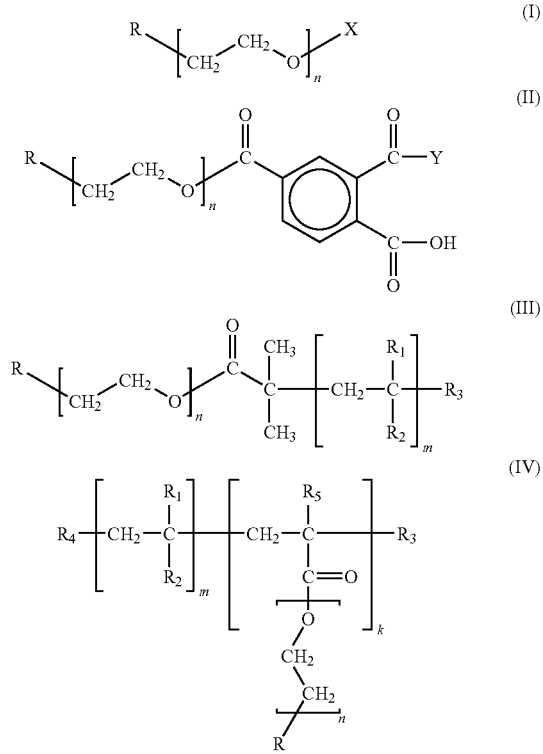

wherein,
R is methyl, n-butyl, sec-butyl or tert-butyl,
$R_1$ and $R_5$ are each independently hydrogen or methyl, $R_2$ is an amide group having a functional group selected from the group consisting of N-isopropylacrylamide, sulfabenzene, sulfioxazole, sulfacetamide, sulfamethizole, sulfadimethoxine, sulfadiazine, sulfamethoxy pyridazine, sulfamethazine, sulfisoimidine, sulfapyridine, indisulam and amprenavir, $R_3$ is hydrogen, isobutylacrylonitryl, phenyl or halogen, $R_4$ is phenyl or isobutylacrylonitryl, X is hydrogen, propylene sulfonic acid, 2-bromoisobutyryl, 2-bromopropionyl, propylene sulfide, methacrylamide or phthalic anhydride, Y is sulfonamide group such as sulfabenzene, sulfioxazole, sulfacetamide, sulfamethizole, sulfadimethoxine, sulfadiazine, sulfamethoxy pyridazine, sulfamethazine, sulfisoimidine, sulfapyridine, indisulam or amprenavir; vitamine group such as folic acid; or drug group such as doxorubicin, paclitaxel or vancomycin;

n is an integer in the range of 10 to 500,
k is an integer in the range of 1 to 10, and
m is an integer in the range of 5 to 50.

The process of the present invention for preparing a nano-sized transition metal or metal salt particle, comprises: a) providing PEO having a specific molecular weight by living polymerization of ethylene oxide using an alkyl lithium as an initiator; b) synthesizing a chain-end functionalized PEO; c) synthesizing a graft or block copolymer in an aqueous solution using the macromonomer or macroinitiator selected from the functionalized PEOs obtained in step b); and d) preparing transition metal or metal salt particles using the polymer obtained in step b) or c).

The chain-end functionalized PEO and the process of preparing nano-sized transition metal or metal salt particles using the same are described in detail below.

First, in anionic living polymerization step a), a living PEO having a number-average molecular weight of 500 to 100,000 g/mol may be obtained by living anionic polymerization of ethylene oxide monomer in a solvent at 20 to 60° C. in the presence of an initiator. The molecular weight of the synthesized PEO can be controlled by varying the ratio of the amount of monomer to the concentration of initiator.

The initiator used in step a) may be an alkyl lithium such as n-butyl lithium, sec-butyl lithium and t-butyl lithium, diiopropylamino lithium, or an alkyl or alkyl alkoxide alkali metal wherein alkali lithium is replaced with an alkali metal such as Na, K, Cs and Rb. Among them, alkyl lithium is preferable. The solvent suitable for use in step a) includes a mixture of dimethyl sulfoxide (DMSO) and a polar (e.g., tetrahydrofuran) or non-polar (e.g., cyclohexane, benzene and toluene) solvent, wherein the volume ratio of the polar or non-polar solvent/DMSO is in the range from 90/10 to 70/30.

The PEO chain-end functionalization step b) may be carried out by reacting the living PEO obtained in step a) with an acid solution (e.g., HCl/methanol and $H_2SO_4$/methanol), sultone (e.g., 1,3-propane sultone and 1,4-butane sultone), ethylene sulfide, propylene sulfide, trimellitic anhydride chloride, methacryloyl chloride, 2-bromoisobutyryl bromide, 2-bromopropionyl bromide or 2-bromopropionyl chloride, etc., under high vacuum.

The solvent used in step b) may be benzene/DMSO or benzene/methanol/DMSO. Also, the functionalization step b) may be conducted at a temperature of 20 to 80° C. for 6 to 48 hours.

Further, in step b), diverse functional groups can be introduced quantitatively into the chain-end of PEO having a specific molecular weight to obtain a chain-end functionalized PEO of formula (I) or (II). The functional groups include, but not limited to: hydroxyl group (—OH), sulfonic acid group (—SO₃H), thiol group (—SH), carboxyl group (—COOH), sulfonamide group (—SO₂NH—); vitamin group such as folic acid; drug group such as doxorubicin, paclitaxel and vancomycin; and sulfonamide-based drug group such as amprenavir.

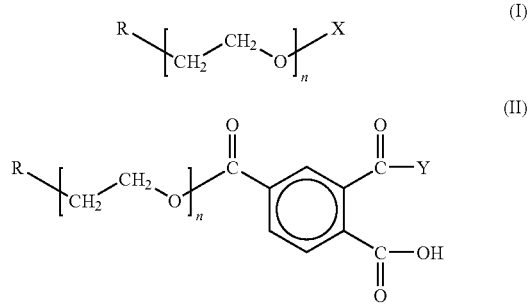

wherein, R, X, Y and n have the same meanings as defined above.

Specifically, for instance, in case of reacting the living PEO obtained in step a) with an acid/methanol mixture, the compound of formula (I) having a chain-end hydroxyl group (—OH) may be obtained, whereas the compound of formula (I) having a chain-end sulfonic acid (—SO₃H) or thiol (—SH) group may be obtained, respectively, by reacting the living PEO with sultone (e.g., 1,3-propane sultone) or propylene sulfide monomer etc., and subsequently with an acid/methanol mixture.

In addition, when the living PEO obtained in step a) is reacted with trimellitic anhydride chloride, followed by reacting the resulting PEO having an anhydride group with vitamin such as folic acid, drug such as doxorubicin, paclitaxel and vancomycin or sulfonamide-based drug such as amprenavir in a solvent, the compound of formula (II) having a chain-end drug group may be obtained.

In step c) for preparing a graft or block copolymer, the PEO-based copolymer of formula (III) or (IV) exhibiting thermo- or pH-responsive properties may be obtained by radical polymerization using the macromonomer or macroinitiator selected from the chain-end functionalized PEOs obtained in step b). Specifically, the block copolymer of formula (III) may be obtained by reacting the macroinitiator (e.g., the compound of formula (I) wherein X is 2-bromoisobutyryl or 2-bromopropionyl) with N-isopropyl acrylamide (NiPAM) or sulfonamide methacrylamide monomer such as sulfadiazine in a solvent in the presence of an initiator. Further, the graft copolymer of formula (IV) may be obtained by reacting the macromonomer (e.g., the compound of formula (I) wherein X is methacrylamide) with NiPAM, or sulfonamide methacrylamide monomer such as sulfadiazine in a solvent in the presence of an initiator (e.g., BPO or AIBN).

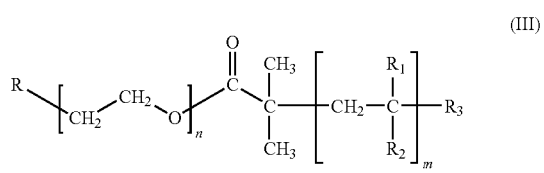

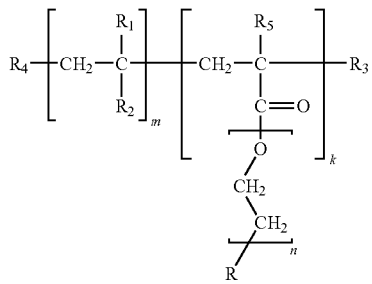

wherein R, R₁, R₂, R₃, R₄, R₅, n, k and m have the same meanings defined above.

The solvent suitable for use in step c) may be water, or a mixture of DMSO and a polar or non-polar solvent as used in step a). The initiator may be benzoyl peroxide (BPO), 2,2'-azobisisobutyronitrile (AIBN) or a copper-based atom transfer radical polymerization (ATRP) catalyst. Also, the radical polymerization step c) may be conducted preferably at a temperature of 20 to 80° C.

Thereafter, in step d), the chain-end functionalized polymer selected from the group consisting of the compounds of formulas (I) to (IV) obtained in steps b) and c) is dissolved in a solvent. An aqueous metal salt solution and a reducing agent are added thereto and allowed to react to obtain polymer-stabilized transition metal or metal salt particles having a nano-size in the range of 1 to 500 nm, preferably 1 to 100 nm.

In step d), the concentration of an aqueous metal salt solution used as a starting material in preparing nano-sized metal or metal salt particles may be preferably in the range of 0.01~10 g/10 ml. The aqueous metal salt solution may be added in an amount to form the molar ratio of polymer to metal salt ranging from 100:1 to 1:1. Further, the reaction temperature may be in the range of 5 to 70° C., preferably 10 to 50° C. The reducing agent includes ammonium hydroxide (NH₄OH), hydrazine monohydrate (N₂H₂), NaBH₄, H₂S, Na₂S etc.

The nano-sized transition metal or metal salt particles prepared in accordance with the present invention include, but not limited to, Au, Ag, Pt(II), Pd(II), CdS, TiO₂, γ-Fe₂O₃ and Fe₃O₄ particles. Also, the size and shape of the obtained metal or metal salt particles may be varied depending on the type of polymer used for stabilization of the particles.

As described above, according to the present invention, various functional groups including a drug can be effectively introduced into PEO having a specific molecular weight. Thus, the nano-sizing of transition metals and their salts such as metal sulfates (e.g., CdS and PbS) and iron oxides (e.g., Fe₃O₄) can be easily achieved. The nano-sized metal or metal salt particles are obtained in a form of polymer-encapsulated particles wherein the polymer is a water-soluble PEO-based material. As such, they can be readily soluble in an aqueous medium as well as in an organic solvent.

That is, the present invention is capable of providing PEO-based polymers having a specific molecular weight and various functional groups at its chain-end via anionic living polymerization and subsequent chain-end functionalization. Also, the present invention is capable of simply preparing nano-sized transition metal or metal salt particles using the PEO-based polymer, wherein the particles are stabilized in water-soluble polymer matrix.

The following Examples are intended to further illustrate the present invention without limiting its scope.

EXAMPLE 1

Each reactant ampoule prepared separately was attached onto 1 L-round bottom Pyrex flask with a hand torch and the air was evacuated therefrom by attaching to vacuum line. n-Butyl lithium (12 mmol) was delivered into the reactor using a syringe under an argon gas atmosphere, cooled to −78° C. using a dry ice/isopropanol bath, followed by removing the argon gas therein using a vacuum pump. Then, 300 ml of purified benzene was distilled to the reactor cooled to −78° C. using a dry ice/isopropanol bath, followed by warming to room temperature to be thoroughly dissolved therein. 30 ml (26.5 g) of purified ethylene oxide (EO, 30 vol. % of dilution solution) was added thereto at 0° C. over an ice bath. To the mixture, 12 mmol of t-BuOK (in 20 ml of THF) and 30 ml of purified dimethyl sulfoxide (DMSO) were further added using a breakseal and stopcock after 1 hr. The mixture was warmed to 35° C. using a water bath, allowed to react at such temperature for 5 hrs, cooled to 5° C. using an ice bath and allowed to react at such temperature for additional 10 minutes. This process was repeated several times. The resulting mixture was stirred for 48 hrs at room temperature and the solvent was removed therefrom by evaporation. The resulting residue was dissolved in THF and precipitated in diethyl ether to obtain poly(ethylene oxide) (PEO). The obtained polymer was dried at room temperature under a vacuum oven for 48 hrs. Gel permeation chromatography (GPC) and $^1$H-NMR analyses were performed. The number-average molecular weight ($M_n$) of the polymer was 2,200 g/mol and the conversion rate of EO to the polymer was not less than 100 mol %.

EXAMPLE 2

20 mmol of 2-bromoisobutyryl bromide (in 20 ml of THF) was added to 200 ml of polymeric alkoxide solution ([POLi]=6.3 mmol) remained in the main reactor before precipitation in Example 1, followed by stirring for 24 hrs at room temperature. After the completion of the reaction, the solvent was removed therefrom by evaporation. The resulting residue was recrystallized from ethanol to obtain powders (PEO-based macro initiator). The number-average molecular weight of the obtained polymer was 2,400 g/mol based on a GPC analysis. The yield of chain-end bromination was over 98 mol % based on a $^1$H-NMR analysis.

EXAMPLE 3

30 mmol of methacrylroyl chloride was added to 200 ml of polymeric alkoxide solution ([POLi]=6.3 mmol) of the living PEO obtained in Example 1, followed by stirring for 24 hrs at room temperature. After the completion of the reaction, the solvent was removed therefrom by evaporation. The resulting residue was re-dissolved in THF, precipitated in diethyl ether and recrystallized from ethanol to obtain the PEO-based macromonomer. The number-average molecular weight of the obtained polymer was 2,300 g/mol based on a GPC analysis. The yield of chain-end functionalization was over 98 mol % based on a $^1$H-NMR analysis.

EXAMPLE 4

1,3-Propane sultone in THF was added ([POLi]/[sultone]=1/3, mol/mol) to 200 ml of polymeric alkoxide solution ([POLi]=6.3 mmol) of living PEO ($M_n$=5,000 g/mol) obtained by performing the similar procedures as in Example 1, followed by stirring for 24 hrs at room temperature to obtain ω-sulfonated PEO. Some of the solvent was removed therefrom by evaporation. The resulting residue was precipitated in diethyl ether, dissolved in THF and recrystallized from ethanol to obtain powders. The number-average molecular weight of the obtained polymer was 5,100 g/mol based on a GPC analysis. The yield of chain-end functionalization was over 99 mol % based on a $^1$H-NMR analysis.

EXAMPLE 5

Purified propylene sulfide was added ([POLi]/[PPS]=1/3, mol/mol) to 200 ml of polymeric alkoxide solution ([POLi]=6.3 mmol) of living PEO ($M_n$=5,000 g/mol) obtained by performing the similar procedures as in Example 1 and allowed to react for 6 hrs at room temperature under a high vacuum to introduce a thiol group into the polymer chain-end. The resulting product was recovered by precipitating it in diethyl ether, re-dissolved in THF and recrystallized from ethanol to obtain as powders. The number-average molecular weight of the obtained polymer was 5,100 g/mol based on a GPC analysis. The yield of chain-end thiolization was over 98 mol % based on a $^1$H-NMR analysis.

EXAMPLE 6

An ampoule containing 0.005 mol of trimellitic anhydride chloride (98%) in 60 ml of THF was prepared, followed by delivering into the main reactor containing the polymeric alkoxide solution ([POLi]=0.001 mmol) of living PEO ($M_n$=3,400 g/mol) obtained by performing the similar procedures as in Example 1 via the breakseal technique. The mixture was allowed to react for 1 hr at 5° C. and was further allowed to react for 15 hrs at 35° C., precipitated in diethyl ether and the solvent was removed therefrom. The resulting residue was dissolved in THF and recrystallized from ethanol to obtain ω-anhydride-PEO. The number-average molecular weight of the obtained polymer was 3,500 g/mol. The yield of chain-end functionalization was about 98 mol % based on the concentration of the polymer solution initially used.

EXAMPLE 7

1.5 g of ω-anhydride-PEO ($M_n$=3,500 g/mol) obtained in Example 6 and doxorubicin chloride (0.24 g)/MeOH (50 ml) were put in 100 ml reactor and allowed to react for 24 hrs under a nitrogen gas atmosphere. The resulting product was recovered by precipitating in dimethyl ether and washed several times using diethyl ether. The precipitates were dissolved in THF, and the THF-soluble and insoluble portions were separated. The THF-soluble portion contains PEO-doxorubicin (PEO-Dox) and the THF-insoluble portion contains unreacted doxorubicin. The THF-soluble portion was concentrated to obtain powders (PEO-Dox) as a dark brown solid. The obtained powder was a polymer drug of PEO having a doxorubicin group at its chain-end. The number-average molecular weight of the obtained polymer was 4,000 g/mol. The yield of chain-end functionalization was over 98 mol % based on a $^1$H-NMR analysis.

EXAMPLE 8

0.01 mol of ω-anhydride-PEO ($M_n$=3,500 g/mol) obtained in Example 6 and sulfamethazine (0.03 mol)/ethanol (50 ml) were put in 250 ml reactor. Then, 100 ml of ethanol was added thereto. The mixture was refluxed for 12 hrs at 70° C. while stirring. After the completion of the reaction, the resulting product was precipitated in diethyl ether at room temperature and recrystallized from ethanol to be obtained in a solid state (PEO-sulfonamide). The number-average molecular weight of the obtained polymer was 4,100 g/mol and the reaction yield was over 98 mol % based on the amount of PEO used.

EXAMPLE 9

1 g of ω-anhydride-PEO ($M_n$=2,000 g/mol) obtained by performing the similar procedures as in Example 6 and 0.88 g of folic acid (5 eq.) were reacted in 20 ml of DMSO for 24 hrs at room temperature. The resulting product was precipitated in diethyl ether, re-dissolved in THF and recrystallized from ethanol to obtain yellow powders (PEO-FA). The number-average molecular weight of the obtained polymer was 2,200 g/mol and the reaction yield was over 98 mol % based on the amount of PEO used.

EXAMPLE 10

Copolymerization of the macromonomer (1.6 mol %) obtained in Example 3 and N-isopropylacrylamide (NiPAM, 98.4 mol %) was performed as follows.

4-(Bromomethyl)benzoic acid (0.25 mmol), sodium hydroxide (0.5 mmol) and distilled water (20 ml) were put in 250 ml 3-neck flask under a nitrogen gas atmosphere. The mixture was slowly stirred for about 30 minutes. The PEO macromonomer (1.15 g, 0.5 mmol)/distilled water (50 ml) solution was prepared in 100 ml 2-neck flask under an argon gas atmosphere. The NiPAM (3.4 g, 30 mmol)/distilled water (50 ml) solution was prepared while stirring in other 100 ml 2-neck flask under an argon gas atmosphere. The $Me_6TREN$ (ligand, 0.25 mmol)/Cu(I)Br (0.25 mmol) mixture was added to the 250 ml flask containing the initiator. Then, the macromonomer and NiPAM solutions were added thereto simultaneously after 1 minute using a cannula and a syringe, respectively. The resulting mixture was stirred for 3 hrs at room temperature under an argon gas atmosphere. The reaction was terminated by adding an excess amount of HCl solution or by exposure to air. The resulting solution was precipitated in distilled water of 50° C. to obtain 4.5 g of powders. The number-average molecular weight of the obtained graft copolymer was 18,000 g/mol.

EXAMPLE 11

Copolymerization of the macromonomer (5 mol %) obtained in Example 3 and sulfonamide methacrylamide monomer (MASX, 95 mol %) was performed as follows.

4-(Bromomethyl)benzoic acid (0.25 mmol), sodium hydroxide (0.5 mmol) and distilled water (20 ml) were put in 250 ml 3-neck flask under a nitrogen gas atmosphere. The mixture was slowly stirred for about 30 minutes. The PEO macromonomer (1.15 g, 0.5 mmol)/distilled water (50 ml) solution was prepared in 100 ml 2-neck flask under an argon gas atmosphere. The sulfonamide methacrylamide monomer (MASX, 3.8 g, 10 mmol)/NaOH (50 mmol)/$H_2O$ (50 ml) solution was prepared in other 100 ml 2-neck flask under an argon gas atmosphere. The $Me_6TREN$ (ligand, 0.25 mmol)/Cu(I)Br (0.25 mmol) mixture was added to the 250 ml flask containing the initiator. Then, the macromonomer and MASX solutions were added thereto simultaneously after 1 minute using a cannula and a syringe, respectively. The resulting mixture was stirred for 3 hrs at room temperature under an argon gas atmosphere. The reaction was terminated by adding an excess amount of HCl solution. The resulting solution was precipitated in distilled water of pH 4.5 to obtain 4.9 g of powders. The number-average molecular weight of the obtained graft copolymer was 19,000 g/mol.

EXAMPLE 12

Atom transfer radical polymerization was performed as follows using the PEO having a chain-end bromide group obtained by performing similar procedures as in Example 2 as an initiator.

$H_2O$/THF (100 ml/10 ml) was put in 250 ml 3-neck flask. Then, 1.25 g of the PEO-based macroinitiator ($M_n$=5,000 g/mol) was added thereto and thoroughly dissolved therewith under an argon gas atmosphere. The MASX (2.6 g, 7 mmol)/NaOH (0.301 g, 7 mmol) mixture was thoroughly dissolved in distilled water (50 ml) in 100 ml 2-neck flask. The $Me_6TREN$ (0.25 mmol)/Cu(I)Br (0.25 mmol) mixture was added to the 250 ml flask and the mixture was stirred for about 10 minutes. To the resulting mixture, the MASX solution was added using a cannula, followed by polymerization for 2 hrs. The polymerization was terminated and the resulting solution was precipitated in an aqueous HCl solution to obtain powders. The powders were washed several times with HCl/methanol and dried in vacuum oven. The number-average molecular weight of the obtained block copolymer was 15,000 g/mol.

EXAMPLE 13

0.15 g of block copolymer (PEO-b-poly(sulfonamide)) obtained in Example 12 was put in 20 ml vial and thoroughly dissolved with 3 ml of DMF (99%). 1 ml of $FeCl_3$ solution (0.146 g of $FeCl_3$/10 ml of DMF) was added thereto using a syringe. The mixture was slowly stirred for 10 minutes using a magnetic bar. The color of the solution in vial was brown. To the mixture, 1 ml of hydrazine monohydrate ($N_2H_2$, Wako Junyaku Co., 98%) was slowly added while stirring until the color thereof does not change any more. When the color change or bubbling no longer occurs, the resulting mixture was precipitated in an excess amount of methanol, filtered, washed and dried to obtain beige powders. The size of the powders was in the range of 2 to 20 nm based on a scanning electron microscopy (SEM) analysis.

EXAMPLE 14

0.51 g of chain-end sulfonated PEO obtained in Example 4 was put in 20 ml vial and thoroughly dissolved with 5 ml of DMF (99%). 2 ml of $FeCl_2$ solution (0.4 g of $FeCl_2$/1 ml of DMF) was added thereto using a syringe. 5 ml of aqueous NaOH solution (12.5 N) was added to the mixture, warmed to 60° C. and stirred. 1.5 ml of $NH_4OH$ was added thereto using a syringe, stirred for 6 hrs, cooled to room temperature and further stirred for 24 hrs. The brown insoluble portion was removed therefrom by filtration and the resulting solution was concentrated under a reduced pressure. The resulting residue was dissolved in methanol and precipitated in dimethyl ether to obtain yellow powders. The size of the powders was in the range of 3 to 10 nm based on a SEM analysis.

EXAMPLE 15

0.51 g of PEO having a chain-end thiol group ($M_n$=5,100 g/mol) obtained in Example 5 was thoroughly dissolved in 10 ml of THF. $HAuCl_4$ ($2.0 \times 10^{-4}$ mol) in 30 ml vial was dissolved with THF (10 ml) and $NaBH_4$ ($1.6 \times 10^{-2}$ mol) dissolved in 10 ml of THF/methanol (9/1, v/v) was added thereto using a syringe. To the mixture, the polymer solution dissolved in THF was added using a syringe, followed by stirring for 24 hrs at room temperature. Some of the solvent was removed therefrom by evaporation and the resulting residue was precipitated in dimethyl ether to obtain light purple powders. The size of the powders was in the range of 2 to 10 nm based on a SEM analysis.

EXAMPLE 16

0.51 g of chain-end sulfonated PEO obtained in Example 4 was put in 20 ml vial and thoroughly dissolved with 5 ml of THF (99%). HAuCl$_4$ (2.0×10$^{-4}$ mol) was injected to 30 ml vial, dissolved with THF (10 ml) and NaBH$_4$ (1.6×10$^{-2}$ mol) dissolved in 10 ml of THF/methanol (9/1, v/v) was added thereto using a syringe. To the mixture, the polymer solution dissolved in THF was added using a syringe, followed by stirring for 24 hrs at room temperature. Some of the solvent was removed therefrom by evaporation and the resulting residue was precipitated in dimethyl ether to obtain light purple powders. The size of the powders was in the range of 3 to 20 nm based on a SEM analysis.

EXAMPLE 17

1.0 g of ω-DOX-PEO (M$_n$=4,000 g/mol) obtained in Example 7 was put in 20 ml vial and thoroughly dissolved with 10 ml of methanol. 1 ml of FeCl$_3$ solution (0.48 g of FeCl$_3$/100 ml of methanol) was added thereto using a pipette. To the mixture, 1 ml of N$_2$H$_2$ was slowly added using a syringe, followed by stirring for 2 hrs. The insoluble portion was removed therefrom by filtration and the resulting solution was precipitated in diethyl ether. It was then washed several times to obtain purple powders. The powders were in the form of nanohybrid having a size ranging from 2 to 20 nm based on a SEM analysis.

EXAMPLE 18

1.5 g of ω-FA-PEO (M$_n$=2,200 g/mol) obtained in Example 9 was dissolved in 50 ml of deoxygenated distilled water. FeCl$_2$/FeCl$_3$ (1 mol/2 mol, 0.4 g/1.0 g) was added thereto and warmed to 80° C. while stirring. To the mixture, 1.5 ml of NH$_4$OH solution was added, followed by stirring for 30 minutes. The resulting mixture was cooled to room temperature and further stirred for 24 hrs. From the resulting solution, the dark brown insoluble portion was removed by filtration and then water was removed. The resulting residue was dissolved in methanol and precipitated in dimethyl ether to obtain yellow powders. The size of the powders was in the range of 2 to 10 nm based on a SEM analysis.

EXAMPLE 19

0.15 g of graft copolymer obtained in Example 11 was put in 20 ml vial and thoroughly dissolved with 3 ml of DMF (99%). 1 ml of FeCl$_3$ solution (0.146 g of FeCl$_3$/10 ml of DMF) was added thereto using a syringe and slowly stirred for about 10 minutes using a magnetic bar. The color of the solution was brown. To the mixture, 1 ml of hydrazine monohydrate (N$_2$H$_2$, Wako Junyaku Co., 98%) was slowly added as a reducing agent while stirring until the color thereof does not change any more. When the color change or bubbling no longer occurs, the resulting solution was precipitated in an excess amount of methanol, filtered, washed and dried to obtain beige powders. The size of the powders was in the range of 3 to 30 nm based on a SEM analysis.

EXAMPLE 20

0.01 mol of ω-anhydride-PEO (M$_n$=3,500 g/mol) obtained in Example 6 and amprenavir (0.03 mol)/ethanol (50 ml) were put in 250 ml reactor and 100 ml of ethanol was added thereto. The mixture was refluxed for 12 hrs at 70° C., precipitated in diethyl ether at room temperature and recrystallized from ethanol to obtain PEO-sulfonamide as a solid. The number-average molecular weight of the obtained polymer was 4,200 g/mol based on a GPC analysis and the reaction yield was over 98 mol % based on the amount of PEO used.

EXAMPLE 21

0.51 g of chain-end sulfonated PEO (M$_n$=5,100 g/mol) obtained in Example 4 was put in 20 ml vial and thoroughly dissolved with 5 ml of toluene/methanol (90/10, v/v). 0.147 g of cadmium acetate hydrate (Cd(OAc)$_2$.xH$_2$O, 6.38×10$^{-4}$ mol) dissolved in 10 ml of toluene/methanol (90/10, v/v) was added thereto. To the mixture, gaseous hydrogen sulfide (H$_2$S) was slowly added using a syringe while stirring until the color thereof changes to yellow. It was then stirred for 6 hours. The resulting mixture was precipitated in diethyl ether to obtain yellow powders. The size of the powders was in the range of 2 to 30 nm based on a SEM analysis.

EXAMPLE 22

The same process as described in Example 21 was repeated except that 0.51 g of PEO having a chain-end thiol group (M$_n$=5,100 g/mol) obtained in Example 5 was put in 20 ml vial and 5 ml of toluene/methanol (90/10, v/v) was added thereto to obtain CdS powders. The size of the powders was in the range of 2 to 30 nm based on a SEM analysis.

EXAMPLE 23

1.5 g of ω-FA-PEO (M$_n$=2,200 g/mol) obtained in Example 9 was dissolved in 50 ml of deoxygenated distilled water, AgNO$_3$ (0.01 mol) was added thereto and warmed to 40° C. while stirring. 1.5 ml of NH$_4$OH solution was added to the mixture, stirred for 30 minutes, cooled to room temperature and allowed to react for 24 hrs while stirring. From the resulting solution, the dark brown insoluble portion was removed by filtration and then water was removed. The resulting residue was dissolved in methanol and precipitated in dimethyl ether to obtain yellow powders. The size of the powders was in the range of 2 to 50 nm based on a SEM analysis.

EXAMPLE 24

2.5 g of ω-thiolated-PEO (M$_n$=5,200 g/mol) obtained in Example 5 was dissolved in 50 ml of deoxygenated distilled water, AgNO$_3$ (0.01 mol) was added thereto and warmed to 40° C. while stirring. To the mixture, 1.5 ml of NH$_4$OH solution was added, followed by stirring for 30 minutes. The resulting mixture was cooled to room temperature and further stirred for 24 hrs. From the resulting solution, the dark brown insoluble portion was removed by filtration and then water was removed. The resulting residue was dissolved in methanol and precipitated in dimethyl ether to obtain yellow powders. The size of the powders was in the range of 2 to 50 nm based on a SEM analysis.

Industrial Applicability

The method of the present invention is capable of simply preparing polymer-drug materials such as a PEO-based polymer and graft or block copolymer exhibiting pH- or thermo-responsive property, wherein various functional materials (e.g., vitamin, anti-cancer agent, sulfonamide material, etc.) are attached to the chain-end of PEO having a specific molecular weight. Further, the method of the present invention is capable of simply preparing nano-sized transition metal or metal salt particles having a size from 1 to 500 nm, preferably 1 to 100 nm, using said various chain-end functionalized PEO-based polymers. Thus, the method of the present invention can be advantageously used in development of new materials which are useful matrices for drug delivering system, e.g., a contrast agent and an anti-cancer agent simultaneously.

The invention claimed is:

1. A nano-particle of a transition metal or salt thereof wherein the transition metal or salt thereof is encapsulated inside a micelle formed by a poly (ethylene oxide) (PEO) having a functionalized chain end selected from the group consisting of compounds of formula (II)

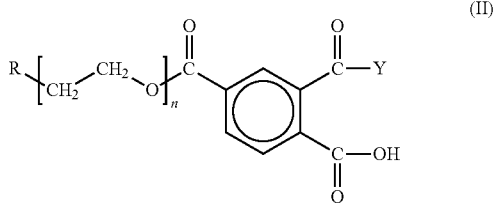

wherein, R is methyl, n-butyl, sec-butyl or tert-butyl, Y is a sulfonamide group selected from the group consisting of sulfabenzene, sulfisoxazole, sulfacetamide, sulfamethizole, sulfadimethoxine, sulfadiazine, sulfamethoxy pyridazine, sulfamethazine, sulfisoimidine, sulfapyridine, indisulam and amprenavir; or vancomycin, and n is an integer in the range of 10 to 500.

2. The nano-particle of a transition metal or salt thereof according to claim 1, wherein the transition metal or salt thereof is selected from the group consisting of Au, Ag, Pt(II), Pd(II), CdS, $TiO_2$, $\gamma$-$Fe_2O_3$ and $Fe_3O_4$.

3. The nano-particle of a transition metal or salt thereof according to claim 1, which has a size in the range of 1 nm to 500 nm.

4. A method of preparing the nano-particle of a transition metal or salt thereof according to claim 1, comprising reacting the poly(ethylene oxide) (PEO) with the transition metal or salt thereof in a solvent under the presence of a reducing agent.

5. The method according to claim 4, wherein the solvent is a polar solvent, a non-polar solvent, or a mixing solvent of a polar solvent and a non-polar solvent.

6. The method according to claim 4, wherein the solvent is water, dimethylformamide (DMF), dimethylsulfoxide (DMSO), tetrahydrofuran (THF), methanol, ethanol or a mixture of toluene and methanol.

7. The method according to claim 4, wherein the poly (ethylene oxide) (PEO) having a functionalized chain end and the transition metal or salt thereof are mixed in a molar ratio of 100:1 to 1:1.

8. The method according to claim 4, wherein the reducing agent is selected from a group consisting of ammonium hydroxide ($NH_4OH$), hydrazine monohydrate ($N_2H_2$), $NaBH_4$, $H_2O_2$, $H_2S$ and $Na_2S$.

9. The method according to claim 4, wherein the poly (ethylene oxide) (PEO) having a functionalized chain end is reacted with the transition metal or salt thereof at a temperature of 5 to 70° C.

* * * * *